United States Patent
Ye et al.

(10) Patent No.: US 10,883,916 B2
(45) Date of Patent: *Jan. 5, 2021

(54) CELL ANALYZER AND SORTING METHOD THEREFOR

(71) Applicant: Shenzhen Mindray Bio-Medical Electronics Co., Ltd., Shenzhen (CN)

(72) Inventors: Bo Ye, Shenzhen (CN); Guanzhen Wang, Shenzhen (CN); Jiantao Di, Shenzhen (CN); Ying Zhang, Shenzhen (CN); Huan Qi, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/801,501

(22) Filed: Feb. 26, 2020

(65) Prior Publication Data
US 2020/0191700 A1    Jun. 18, 2020

Related U.S. Application Data

(63) Continuation of application No. 16/414,023, filed on May 16, 2019, now Pat. No. 10,627,332, which is a
(Continued)

(51) Int. Cl.
*G01N 15/14* (2006.01)
*G01N 21/64* (2006.01)
(Continued)

(52) U.S. Cl.
CPC ......... *G01N 15/1459* (2013.01); *G01N 15/14* (2013.01); *G01N 15/1429* (2013.01); (Continued)

(58) Field of Classification Search
CPC ............... G01N 15/1459; G01N 15/14; G01N 15/1429; G01N 21/53; G01N 21/6428;
(Continued)

(56) References Cited

U.S. PATENT DOCUMENTS 5,757,475 A    5/1998  Katayama et al.
8,772,738 B2   7/2014  Ozasa et al.
(Continued)

FOREIGN PATENT DOCUMENTS

CN    1159584 A      9/1997
CN    101498646      8/2009
(Continued)

*Primary Examiner* — Jamil Ahmed
(74) *Attorney, Agent, or Firm* — Kory D. Christensen

(57) ABSTRACT

A cell analyzer and a sorting method for the cell analyzer are disclosed. Multiple optical signals generated by each of particles irradiated with light in a blood sample in a detection region are collected. The particles includes a first category of particles and a second category of particles. For each of the particles, Intensities of a first group of optical signals, which includes at least two optical signals selected from the multiple optical signals, and a pulse width of a second group of optical signals, which includes at least one optical signal selected from the multiple optical signals are acquired. For each of the particles, one or more reinforcement signals related to the particle are calculated based on an intensity of a first optical signal selected from the first group of optical signals and a pulse width of a second optical signal selected from the second group of optical signals, where the first optical signal is as same as or different from the second optical signal. The first category of particles and the second category of particles are distinguished from each other based at least partially on the one or more reinforcement signals related to each of the particles.

18 Claims, 13 Drawing Sheets

Related U.S. Application Data continuation of application No. 15/675,079, filed on Aug. 11, 2017, now Pat. No. 10,330,584, which is a continuation of application No. PCT/CN2015/072907, filed on Feb. 12, 2015.

(51) Int. Cl.
*G01N 21/53* (2006.01)
*G01N 33/49* (2006.01)
*G01N 15/00* (2006.01)
*G01N 15/10* (2006.01)

(52) U.S. Cl.
CPC .......... *G01N 21/53* (2013.01); *G01N 21/6428* (2013.01); *G01N 33/49* (2013.01); *G01N 2015/008* (2013.01); *G01N 2015/1006* (2013.01); *G01N 2015/149* (2013.01); *G01N 2201/12* (2013.01)

(58) Field of Classification Search
CPC ............. G01N 33/49; G01N 2015/008; G01N 2015/1006; G01N 2015/149; G01N 2201/12; G01N 15/02; G01N 21/00; G01N 21/05; G01N 21/49; G01N 21/64; G01N 1/31; G01N 33/50; C12Q 1/68; C12Q 1/02; C12Q 1/04; C12M 1/34; G01J 1/58; G06F 19/00
See application file for complete search history.

(56) References Cited

U.S. PATENT DOCUMENTS

| | | | |
|---|---|---|---|
| 2008/0176274 A1* | 7/2008 | Tsuji | G01N 33/52 435/34 |
| 2009/0323062 A1 | 12/2009 | Ariyoshi et al. | |
| 2010/0196917 A1 | 8/2010 | Ishisaka et al. | |
| 2011/0127444 A1 | 6/2011 | Ozasa et al. | |
| 2012/0295339 A1 | 11/2012 | Wu et al. | |
| 2014/0154677 A1 | 6/2014 | Ishisaka et al. | |

FOREIGN PATENT DOCUMENTS

| | | |
|---|---|---|
| CN | 101620223 A | 1/2010 |
| CN | 101842688 A | 9/2010 |
| CN | 102156088 A | 8/2011 |

\* cited by examiner

CELL ANALYZER AND SORTING METHOD THEREFOR

CROSS-REFERENCE TO RELATED APPLICATIONS

This application is a continuation of U.S. patent application Ser. No. 16/414,023, filed on May 16, 2019, which is a continuation of U.S. patent application Ser. No. 15/675,079, filed on Aug. 11, 2017, for "Cell Analyzer and Particle Soring Method and Device," which is a continuation of PCT App. No. PCT/CN2015/072907, filed on Feb. 12, 2015, for "Cell Analyzer and Particle Sorting Method and Device," each of which are incorporated herein by reference.

TECHNICAL FIELD

The present disclosure relates to a medical devices, and more particularly to a cell analyzer and sorting method for the cell analyzer.

BACKGROUND

A blood cell analyzer is an instrument that detects cells in the blood. It counts and sorts cells such as leucocytes (white blood cells or WBC), red blood cells, blood platelets, nucleated red blood cells and reticulocytes.

The most common cell analyzer used by a blood cell analyzer to detect leucocytes is a laser scattering cell analyzer, in which, by irradiating cell particles flowing through a detection region with light, optical signals reflected or scattered by various categories of particles are collected, and then the optical signals are processed and analyzed so as to sort and count the leucocytes. The collected optical signals may include three types of optical signals, including forward-scattered light, side-scattered light, and fluorescence signals. The forward-scattered light can reflect size information of the cell, the side-scattered light can reflect complexity of an internal structure of the cell, and the fluorescence signal reflects components in the cell that can be dyed by a fluorescent dye, such as DNA and RNA. By means of these optical signals, the leucocytes can be sorted, and the leucocyte count can be obtained at the same time.

According to different pretreatments of blood samples (e.g., reagents being different), detection processes are divided into different detection channels, such as a differential (DIFF) channel, a basophil (BASO) channel and a nucleated red blood cell (NRBC) channel. The BASO channel is used to sort and count leucocytes, while a blood sample is treated with a chemical reagent, the total number of leucocytes is counted by means of side-scattered light and forward-scattered light, and a count of basophil granulocytes in the leucocytes is also provided. The NRBC channel can be used to sort nucleated red blood cells after a blood sample is treated with a fluorescent reagent added therein. The NRBC channel can provide a leucocyte count and a nucleated red blood cell count.

During blood cell detection by a blood cell analyzer, two types of particles cannot be clearly distinguished from each other in some cases, thus affecting particle sorting results. For example, when counting leucocytes, the leucocytes may not be counted accurately due to the influence of interfering particles. The interfering particles may include lipid granules or aggregated PLT (blood platelet) particles. PLT is a part of a blood ghost which is a cell debris structure formed after a sample pretreatment of a blood sample, in which cells such as red blood cells or platelets are subjected to a hypotonic treatment or treated with a reagent, resulting in cell membrane rupture. Generally, the particle size is small, and the forward-scattered light signal is weak. However, in some samples, PLT aggregation may occur and interfering with the leucocyte detection. These interfering particles may overlap with the leucocyte in the scatter diagram. FIG. 1 shows a detection result of the NRBC channel, where an aggregated platelet cluster A1 overlaps with a leucocyte cluster B1 in the forward-scattered light and fluorescence signals. FIG. 2 shows a detection result of the BASO channel, where leucocytes are sorted into a basophil granulocyte cluster A2 and a cluster B2 of other leucocyte particles including lymphocytes, monocytes, neutrophil granulocytes and eosinophil granulocytes. Due to the existence of lipid particles, a lipid granule cluster C2 overlaps with the cluster B2 of other leucocyte particles in a region D2 at a lower end of the forward-scattered light and side-scattered light signals, which may interfere with counting of leucocytes. It can be seen that the existence of these interfering particles in the blood sample will affect the accuracy of the detection results.

BRIEF SUMMARY

According to a first aspect, a sorting method for a cell analyzer is provided. The method includes actions of collecting multiple optical signals generated by each of particles irradiated with light in a blood sample in a detection region, the particles comprising a first category of particles and a second category of particles; for each of the particles, acquiring intensities of a first group of optical signals, which comprise at least two optical signals selected from the multiple optical signals, and a pulse width of a second group of optical signals, which comprises at least one optical signal selected from the multiple optical signals; for each of the particles, calculating one or more reinforcement signals related to the particle, based on an intensity of a first optical signal selected from the first group of optical signals and a pulse width of a second optical signal selected from the second group of optical signals, wherein the first optical signal is as same as or different from the second optical signal; and distinguishing between the first category of particles and the second category of particles based at least partially on the one or more reinforcement signals related to each of the particles.

According to a second aspect, a cell analyzer is provided. The cell analyzer includes a reaction chamber, a flow chamber, a conveying apparatus, an optical detection apparatus, and a data processing apparatus. The reaction chamber provides a location for reaction between a blood sample and a reagent to get a sample liquid. The flow chamber has a detection region, through which the sample liquid pass in sequence with shrouding by a sheath liquid. The conveying apparatus has a conveying line and a control valve, wherein the sample liquid is conveyed into the flow chamber through the conveying line. The optical detection apparatus has a plurality of optical signal detectors, operable to collect multiple optical signals generated by each of particles irradiated with light in a blood sample in a detection region, the particles comprising a first category of particles and a second category of particles. The data processing apparatus is configured to, for each of the particles, acquire intensities of a first group of optical signals, which comprise at least two optical signals selected from the multiple optical signals, and a pulse width of a second group of optical signals, which comprises at least one optical signal selected from the multiple optical signals; for each of the particles, calculate one or more reinforcement signals related to the particle, each reinforcement signal comprising a reinforcement signal based on an intensity of a first optical signal selected from the first group of optical signals and a pulse width of a second optical signal selected from the second group of optical signals, wherein the first optical signal is as same as or different from the second optical signal; and distinguish between the first category of particles and the second category of particles based at least partially on the one or more reinforcement signals.

According to a third aspect, a sorting method for a cell analyzer is provided. The method includes actions of collecting multiple optical signals generated by each of particles irradiated with light in a blood sample in a detection region, the particles comprising a first category of particles and a second category of particles, and the multiple optical signals comprising a forward-scattered light signal and a side-scattered light signal; for each of the particles, acquiring intensities of the forward-scattered light signal and the side-scattered light signal, and a pulse width the forward-scattered light signal; for each of the particles, calculating a reinforcement signal related to the particle, based on the intensity of the forward-scattered light signal and the pulse width of the forward-scattered light signal; generating a first scatter diagram for the particles based on the reinforcement signal related to each of the particles and the intensity of the side-scattered light signal of the respective particle; and distinguishing between the first category of particles and the second category of particles based on the first scatter diagram, wherein the first category of particles are leucocyte particles, and the second category of particles are lipid granules.

According to a fourth aspect, a sorting method for a cell analyzer is provided. The method includes actions of collecting multiple optical signals generated by each of particles irradiated with light in a blood sample in a detection region, the particles comprising a first category of particles and a second category of particles, and the multiple optical signals comprising a fluorescence signal and at least one scattered light signal; for each of the particles, acquiring intensities of a first optical signal and a second optical signal selected from the multiple optical signals and a pulse width of a third optical signal selected from the multiple optical signals, the first optical signal being different from the second optical signal, and the third optical signal being as same as or different from the first optical signal or the second optical signal; for each of the particles, calculating a reinforcement signal related to the particle, based on the intensity of the first optical signal and the pulse width of the third light signal; generating a first scatter diagram for the particles based on the reinforcement signal and the intensity of the second optical signal of each of the particles; and distinguishing between the first category of particles and the second category of particles based on the first scatter diagram.

According to a fifth aspect, a non-transitory computer readable storage medium is provided, in which instructions are stored. The instructions, when executed by a processor, cause the processor to execute the method according to the first aspect.

DETAILED DESCRIPTION

Figure 3:
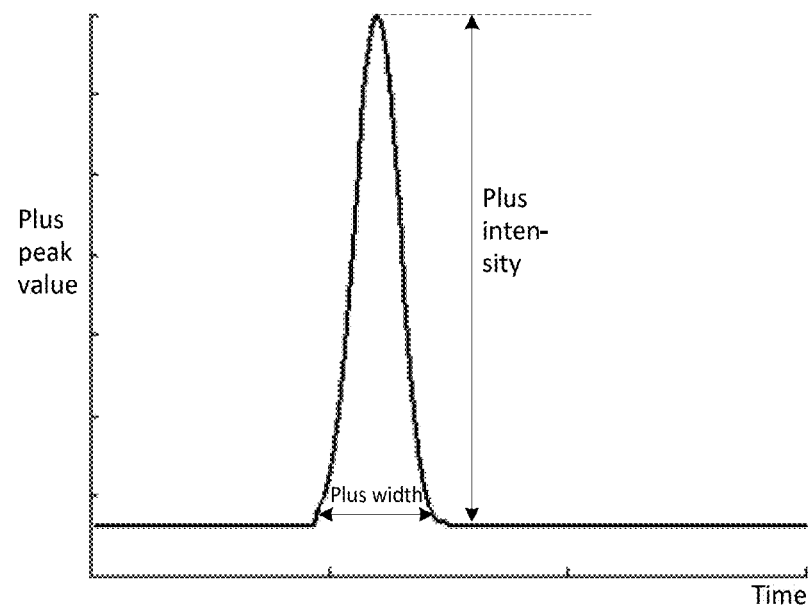
FIG. 3 is a schematic diagram of a detected pulse.

A particle passing through a detection region generates a pulse, and the width of the pulse (hereinafter referred to as pulse width) can reflect the time during which the particle passes through the detection region, and thus can characterize the size of the particle. FIG. 3 shows a schematic diagram of a detected pulse, where a pulse signal is excited when a particle passes through a detection region. The pulse width is from the start of the pulse to the end of the pulse, and the pulse width signal is the time during which the particle passes through the detection region. When the flow rate is constant, the smaller the particle is, the shorter the time will be during which the particle passes through the detection region is, and in turn the smaller the corresponding pulse width will be. By contrast, the larger the particle is, the longer the time during which the particle passes through the detection region, and in turn the greater the corresponding pulse width will be. Therefore, it is theoretically possible to distinguish between different kinds of particles by pulse width.

In a sample where platelet aggregation occurs, the width of a pulse generated by aggregated particles when passing through the detection region is relatively large. It is theoretically possible to distinguish between aggregated blood platelet particles and leucocytes by pulse width. However, due to the fact that the number of blood platelets aggregated together is different, the blood platelet clusters range widely in particle size, some aggregated blood platelet particles of a larger size will overlap with leucocyte groups. Therefore, the leucocytes and the aggregated blood platelet particles cannot be perfectly distinguished from each other by pulse width.

Figure 4A:
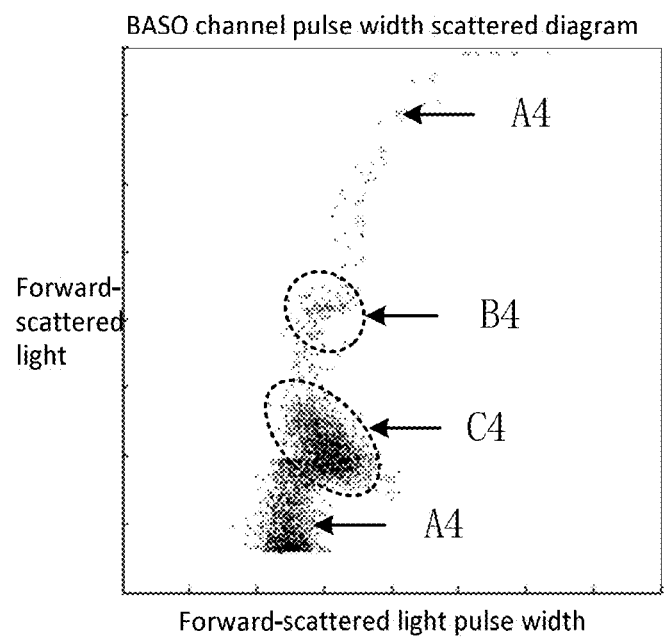
FIG. 4a is a forward-scattered pulse width-forward-scattered light scatter diagram of the lipid granule sample.
Figure 4B:
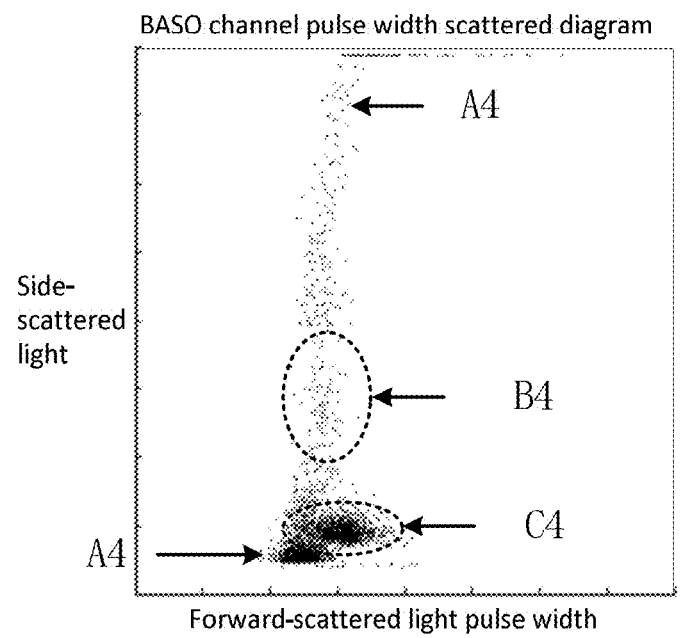
FIG. 4b is a forward-scattered pulse width-side-scattered light scatter diagram of the lipid granule sample.

With regard to lipid granules in a blood sample, because the size thereof varies, the volume thereof presents a variation from small to large magnitudes in each case. For lipid granule particles of small diameters, the corresponding pulse width is small; and for lipid granule particles of large diameters, the corresponding pulse width is large. In the case of a small pulse width, it is possible that the pulse width of a lipid granule is equal to that of a leucocyte. As shown in FIGS. 4A and 4B, it can be seen that a lipid granule cluster A4 has from small to large pulse widths, and overlaps with a basophil granulocyte cluster B4 and a cluster C4 of other leucocyte particles in the small pulse width part. Consequently, the lipid granules and the leucocytes cannot be separated from each other favorably according to pulse width, whether based on a forward-scattered light scatter diagram or on a side-scattered light scatter diagram.

Therefore, in embodiments of the present disclosure, according to the difference in pulse width between the interfering particles and the leucocyte particles, a new reinforcement signal is formed by combining a function of an optical signal with a function of the pulse width signal, so that a scatter diagram generated based on the reinforcement signal can significantly enhance the effect of separating particle groups.

In the present disclosure, a new reinforcement signal is formed by combining a function of a certain optical signal and a function of a pulse width signal so that the difference between the first category of particles and the second category of particles in the reinforcement signal is increased, and a new scatter diagram is generated based on the reinforcement signal. By means of the greater difference between the first category of particles and the second category of particles in the reinforcement signal, the first category of particles and the second category of particles can be distinguished from each other, thereby improving the accuracy of particle sorting.

As those skilled in the art would understand, the scatter diagram is merely a data representation form. The scatter diagrams in the present disclosure are not limited to the graphic presentation form. For example, the scatter diagram may be in a data form. In some embodiments of the disclosure, no scatter diagram is generated. Instead, the first category of particles and the second category of particles can be distinguished from each other based on the reinforcement signal by using other data analysis approaches.

Figure 5:
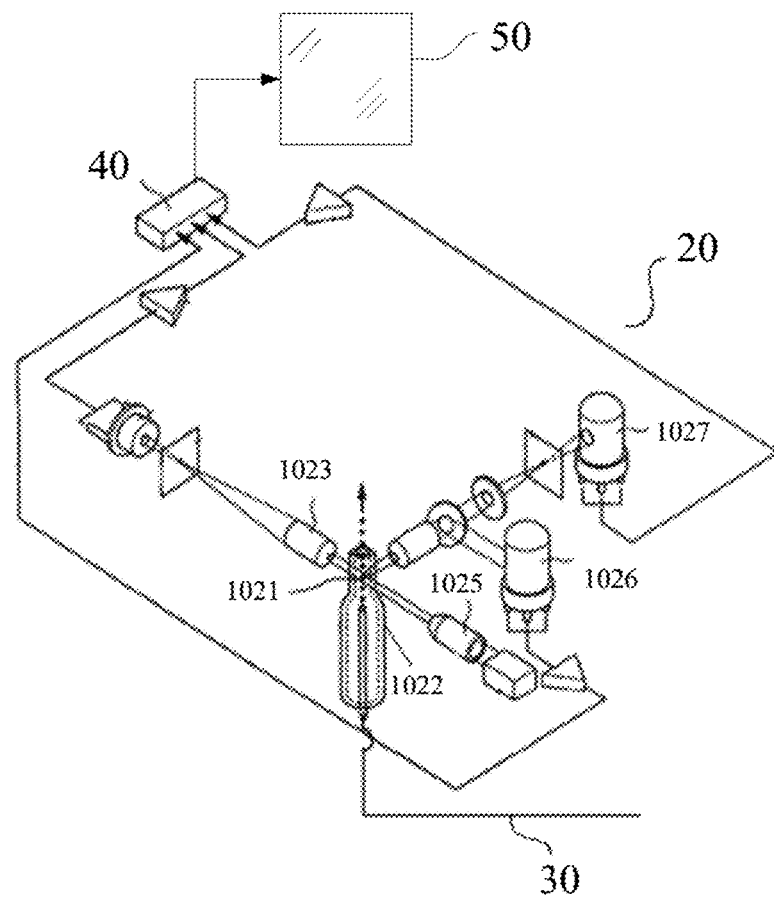
FIG. 5 is a structural schematic diagram of a blood cell analyzer.

FIG. 5 shows a structural schematic diagram of a blood cell analyzer. The blood cell analyzer comprises an optical detection apparatus 20, a conveying apparatus 30, a data processing device 40 and a display apparatus 50.

The conveying apparatus 30 conveys a sample liquid (e.g., a blood sample to be tested) after reaction with a reagent to the optical detection apparatus 20. The conveying apparatus 30 typically comprises a conveying line and a control valve, where the sample liquid is conveyed into the optical detection apparatus 20 through the conveying line and the control valve.

Figure 20A:
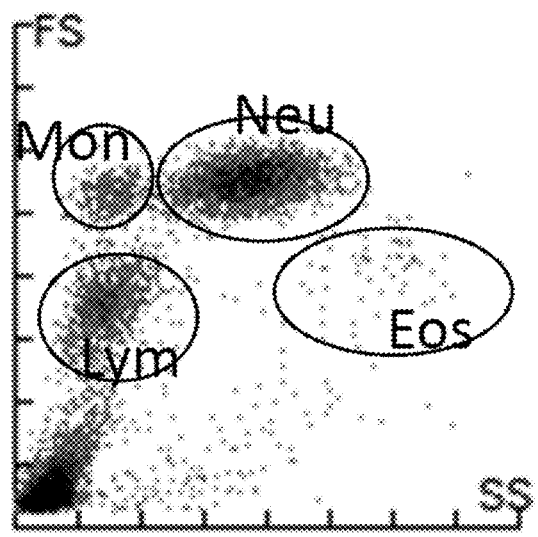
FIG. 20A is a scatter diagram with the forward-scattered light signal and the side-scattered light signal showing four-classification of the leucocytes.
Figure 20B:
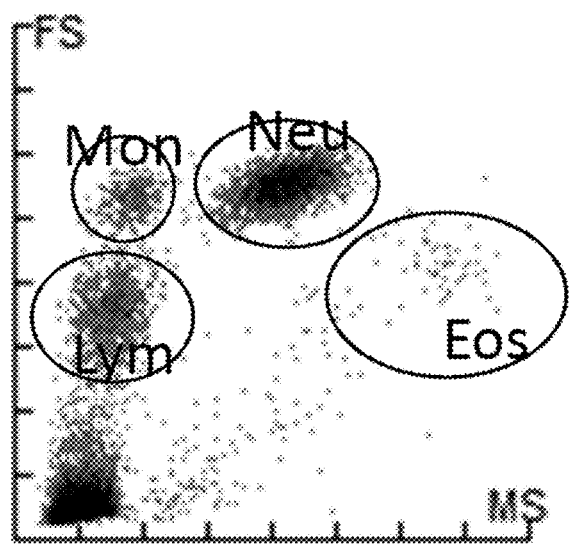
FIG. 20B is a scatter diagram with the forward-scattered light signal and the medium-angle-scattered light signal showing four-classification of the leucocytes.

The optical detection apparatus 20 irradiates the sample liquid flowing through the detection region thereof with light, collecting various optical information (e.g., scattered light information and/or fluorescence information) generated by cells irradiated with light, and converting the optical information into corresponding electric signals. The information corresponds to the characteristics of the cell particles and can be used as characteristic data of the cell particles. The forward-scattered light signal reflects size information of the cell, the side-scattered light signal reflects complexity of an internal structure of the cell, and the fluorescence signal reflects the component in the cell that can be dyed by a fluorescent dye, such as DNA and RNA. In the embodiment shown in FIG. 5, the optical detection apparatus 20 can include a light source 1025, a detection region 1021 serving as the detection region, a forward-scattered light signal collecting device 1023 provided on an optical axis, a side-scattered light signal collecting device 1026 and a fluorescence signal collecting device 1027 provided at a side of the optical axis. In some embodiments, the fluorescence signal collecting device 1027 is not required. Instead, the fluorescent signal collecting device 1027 includes a forward-scattered light collecting device 1023, a side-scattered light collecting device, and a medium-angle-scattered light collecting device for collecting a medium-angle-scattered light signal at an angle between the forward-scattered light (FS) and the side-scattered light(SS), which may be a low-medium-angle-scattered light signal at an angle of about 8° to about 24° to the incident beam, or a high-medium-angle-scattered light signal at an angle of about 25° to the incident beam. In FIG. 20A and FIG. 20B, a comparison is performed between classification of leucocyte particles based on the forward-scattered light signal (FS)—side-scattered light signal (SS) scatter diagram, and classification of leucocyte particles based on the forward-scattered light signal (FS)—high-medium-angle-scattered light signal (MS). The classifications of the leucocyte particles on the scatter diagrams show that both can distinguish leucocyte particles into four categories. It indicates that the medium-angle-scattered light signal can be used as a combined signal, or a pulse signal of the medium-angle-scattered light signal can be used in combination with a combined signal to calculate a reinforcement signal, or the medium-angle-scattered light signal can be used in combination with a reinforcement signal to generate a new scatter diagram.

A blood sample is separated as needed. A part of the blood sample reacts with a reagent in a reaction chamber (not shown) to get a sample liquid. Particles in the sample liquid pass through the detection region 1021 of a flow chamber 1022 in sequence with shrouding by a sheath liquid. A light beam emitted by the light source 1025 is projected to the detection region 1021. Cell particles in the sample liquid are irradiated with the light beam and then emit scattered light. The light collecting device collects the scattered light, and the collected and shaped light is projected to a photoelectric sensor. The photoelectric sensor converts the optical signal into a corresponding electrical signal and outputs the electrical signal to the data processing device 40.

The data processing device 40 is configured to receive optical information output from the optical detection apparatus 20, where the optical information of each particle is used as a characteristic data set characterizing the particle, and an analysis of the blood sample is realized by analyzing and processing the characteristic data of the particles. In one embodiment, the data processing device 40 includes a particle sorting device that generates a desired scatter diagram based on the characteristic data sets of the particles and sorts the particles according to the scatter diagram. In some embodiments, the particle sorting device distinguishes leucocytes from interfering particles, where the interfering particles may be aggregated blood platelet particles or lipid granules. In some embodiments, the scatter diagram refers to a set of characteristic data sets of the cell particles, which may be stored in a storage device in a digitized form, or may be presented in a visualized form on a display interface.

The display apparatus 50 is electrically coupled to the data processing device 40 to display the analysis result output by the data processing device 40, and the analysis result may be a graphic, a text description, a table, and/or the like. In one embodiment, the display apparatus 50 may output various visualized scatter diagrams and/or various cell sorting results.

Figure 6:
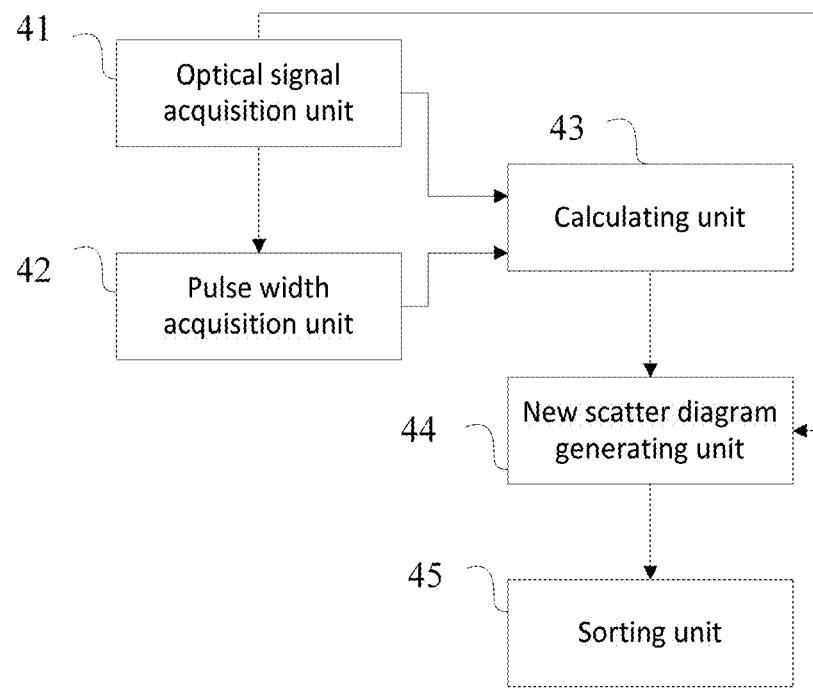
FIG. 6 is a structural schematic diagram of a particle sorting device.

In one embodiment, leucocyte particles and interfering particles are distinguished from each other by means of reinforcement signals of optical signals and pulse width signals, regardless of the presence or absence of the interfering particles and whether or not the interfering particles overlap with the leucocytes. As shown in FIG. 6, a particle sorting device includes an optical signal acquisition unit 41, a pulse width acquisition unit 42, a calculating unit 43, a new scatter diagram generating unit 44 and a sorting unit 45. These and the other units described herein may be implemented using any combination of hardware, software, and/or firmware.

The optical signal acquisition unit 41 acquires an optical signal. When the blood sample passes through a detection region, the detection region is irradiated with light emitted by the optical detection apparatus 20, and particles in the sample are irradiated with the light to generate corresponding optical signals. The optical detection apparatus 20 collects various optical information generated by the particles due to the light irradiation. The optical signals include at least two of forward-scattered light, side-scattered light and fluorescence, for example, forward-scattered light and side-scattered light, or the forward-scattered light, the—side scattered light and the fluorescence.

The pulse width acquisition unit 42 acquires a pulse width of at least one optical signal. In some embodiment, the pulse width acquisition unit 42 selects an optical signal from the collected optical signals and records the pulse width of this optical signal, for example, it can record the pulse width of the forward-scattered light, the side-scattered light or the fluorescence. In another particular embodiment, the pulse width acquisition unit 42 selects a plurality of optical signals from the collected optical signals and records the pulse width of each of the plurality of optical signals, for example, the pulse widths of both the forward-scattered light and the fluorescence.

The calculating unit 43 calculates a reinforcement signal. The reinforcement signal is calculated from the pulse width of an optical signal and a combined optical signal using a combinatorial function. The combined optical signal may be any one of the optical signals obtained by the optical signal acquisition unit 41. The combinatorial calculation increases the difference in the reinforcement signal between the leucocyte particles and the interfering particles relative to the difference between the two in the combined optical signal.

For example, the reinforcement signal may be a function of the combined optical signal and the pulse width, which has an expression as follows:

$$Z = f(X, Y) \quad (1)$$

where Z is the reinforcement signal; f is the function; X is the intensity of the combined optical signal, where in some embodiments, the intensity of an optical signal can be the peak value of the optical pulse signal; and Y is the pulse width.

According to expression (1) above, the function f has the following characteristics:

the function f is monotonic for the combined optical signal or pulse width, i.e., when the combined optical signal is fixed (or constant), the function is a monotonic function for the pulse width, for example, the function is an increasing or decreasing function of the pulse width; and when the pulse width is fixed, the function is a monotonic function for the combined optical signal, for example, the function is an increasing or decreasing function of the combined optical signal.

Alternatively, the function f has the following characteristics: the function f is a non-linear combinatorial function of the combined optical signal and the pulse width.

In some embodiments, the reinforcement signal obtained through the combinatorial calculation by the calculating unit 43 may comprise one signal, for example, the reinforcement signal is only a reinforcement signal of the forward-scattered light with the pulse width. The reinforcement signal obtained through combinatorial calculation by the calculating unit 43 may comprise a plurality of types of signals. For example, the reinforcement signal may be a reinforcement signal of the forward-scattered light with the pulse width, combined with a reinforcement signal of the side-scattered light with the pulse width. In some embodiments, the optical signal of which the pulse width is recorded and the combined optical signal may be the same optical signal or may be different optical signals.

The new scatter diagram generating unit 44 forms a new scatter diagram on the basis of the reinforcement signal and at least another signal, and the at least another signal may be at least one optical signal different from the combined optical signal, or at least one of or a combination of two other reinforcement signals. The new scatter diagram may be two-dimensional or three-dimensional, where at least one dimension is the reinforcement signal.

In some embodiments, a new scatter diagram is formed by selecting an optical signal and a reinforcement signal, for example, selecting one optical signal and one reinforcement signal to form a two-dimensional new scatter diagram, or selecting one optical signal and two reinforcement signals to form a three-dimensional new scatter diagram, or selecting two optical signals and one reinforcement signal to form a three-dimensional new scatter diagram.

In some implementations, an optical signal may be selected that is different from the combined optical signal and a reinforcement signal to form a new scatter diagram. For example, if the combined optical signal for calculating the reinforcement signal is fluorescence, the forward-scattered light and the reinforcement signal are selected to form a new scatter diagram.

In another particular embodiment, a certain reinforcement signal and other reinforcement signals are selected to form a new scatter diagram, where the other reinforcement signals refer to a reinforcement signal different from the certain reinforcement signal, for example, selecting an A-type reinforcement signal from the at least one reinforcement signal calculated by the calculating unit 43 as a dimension of the new scatter diagram, and then selecting a B-type reinforcement signal different from the A-type reinforcement signal as another dimension of the new scatter diagram. In other words, the new scatter diagram selects two types of reinforcement signals to form a two-dimensional new scatter diagram, e.g., selecting a reinforcement signal of the forward-scattered light and the pulse width, and a reinforcement signal of the side-scattered light and the pulse width to form a two-dimensional new scatter diagram.

The sorting unit 45 distinguishes between the leucocyte particles and the interfering particles according to the new scatter diagram. Leucocyte particles and interfering particles differ slightly in optical signal and pulse width, but the difference is not sufficient to distinguish between the leucocyte particles and the interfering particles. The difference can be increased by a combinatorial calculation of the optical signals and the pulse width. Since the reinforcement signal increases the difference in the reinforcement signal between the leucocyte particles and the interfering particles relative to the difference between the two in the combined optical signal, the leucocyte particles and the interfering particles can be distinguished from each other in a scatter diagram based at least on the reinforcement signal.

In another embodiment, a conventional cell analyzer is used first, i.e., a scatter diagram is generated based on an optical signal, which is referred to as an initial scatter diagram. When there is an overlap region in the initial scatter diagram between leucocyte particles and interfering particles, a reinforcement signal of the optical signal and the pulse width signal are used then to distinguish between the leucocyte particles and the interfering particles.

Figure 7:
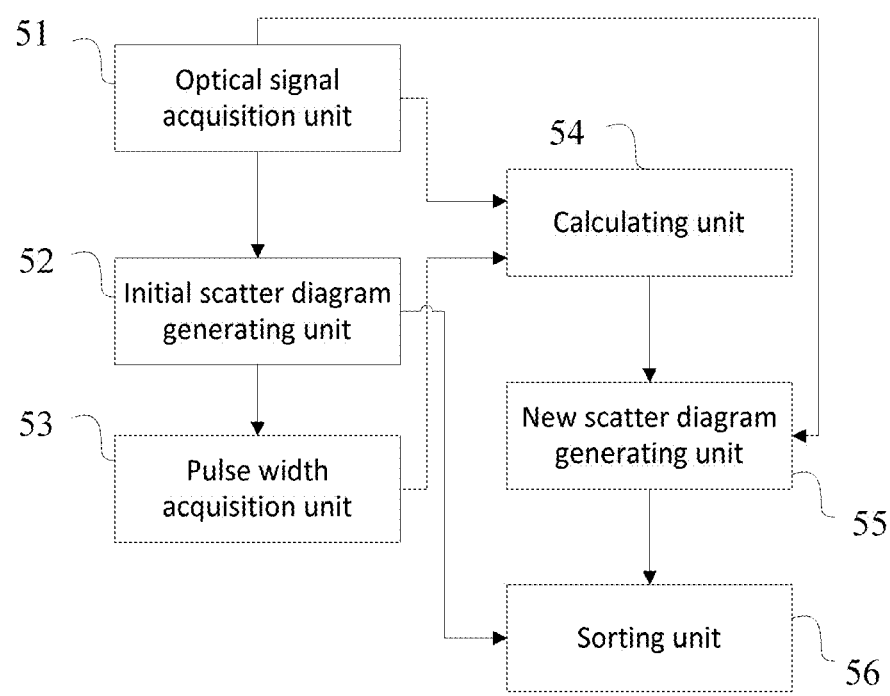
FIG. 7 is a structural schematic diagram of a particle sorting device.

As shown in FIG. 7, a particle sorting device includes an optical signal acquisition unit 51, an initial scatter diagram generating unit 52, a pulse width acquisition unit 53, a calculating unit 54, a new scatter diagram generating unit 55 and a sorting unit 56. The optical signal acquisition unit 51, the calculating unit 54 and the new scatter diagram generating unit 55 may be the same as those in the foregoing embodiment. The initial scatter diagram generating unit 52 generates an initial scatter diagram for sorting and/or counting the leucocytes according to an optical signal. The pulse width acquisition unit 53 acquires a pulse width of at least one optical signal when there is an overlap region between a leucocyte particle cluster and an interfering particle cluster in the initial scatter diagram. The sorting unit 56 distinguishes between the leucocyte particles and the interfering particles and counting the leucocytes according to the new scatter diagram. When the leucocyte particle cluster and the interfering particle cluster have no overlap regions in the initial scatter diagram, the sorting unit 56 also counts the leucocytes according to the initial scatter diagram.

The following disclosure relates to embodiments of specific blood samples.

In one embodiment, a blood platelet aggregation sample is taken as an example, the blood sample was measured by a blood cell analyzer, and a leucocyte count can be obtained through an NRBC channel.

Figure 8:
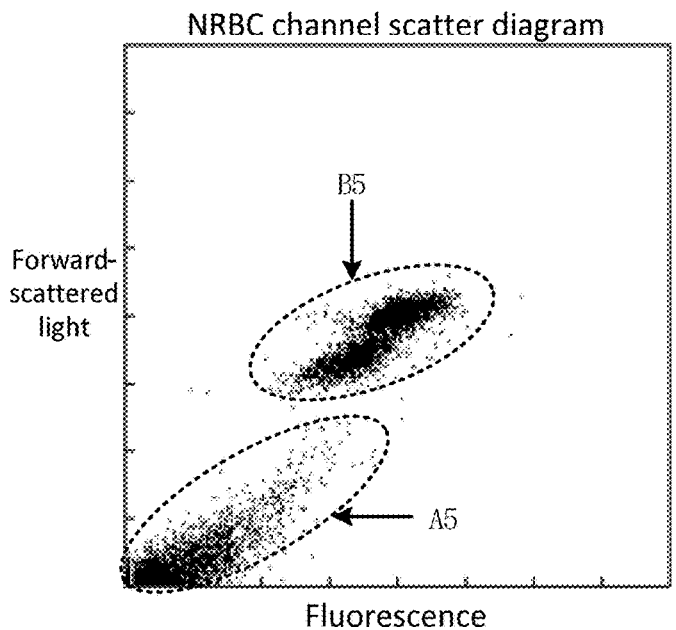
FIG. 8 is an NRBC channel scatter diagram of a normal sample.

In general, red blood cells and blood platelets will form cell debris after being treated with a hemolytic agent, and the cell debris will be located in a part of lower-end signals in the NRBC channel after measurement by the blood cell analyzer. A NRBC channel scatter diagram of a normal sample is shown in FIG. 8. It can be seen that the blood ghost A5 and leucocyte cluster B5 are significantly separated from each other, so that the blood ghost will not interfere with the leucocyte counting.

Figure 1:
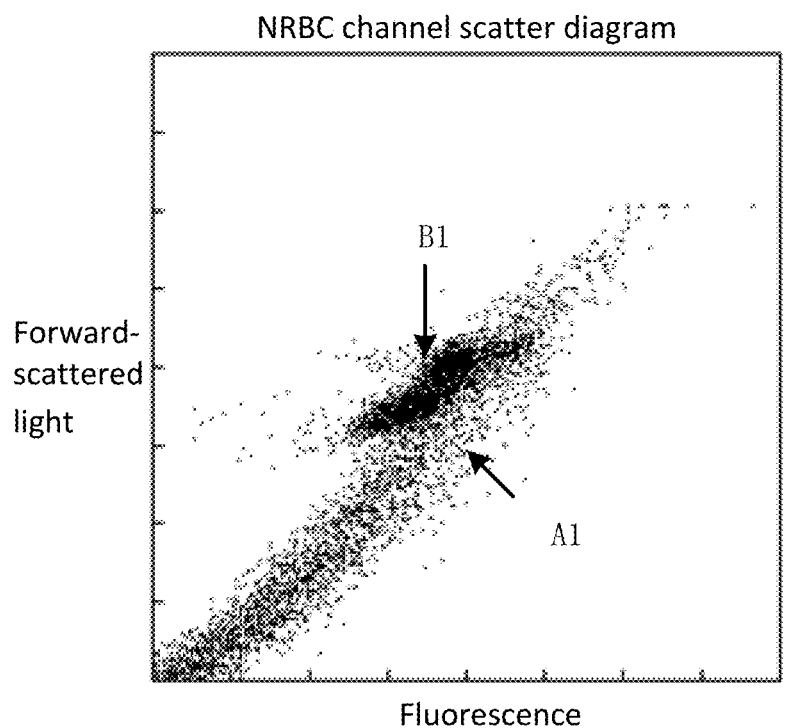
FIG. 1 is an NRBC channel scatter diagram of a blood platelet aggregation sample.

When there is blood platelet aggregation in a blood sample, the hemolytic agent cannot dissolve the blood platelet favorably, so that aggregated blood platelets may remain in the blood sample, and the aggregated blood platelets have a high signal intensity and will overlap with a leucocyte group. As shown in FIG. 1, aggregated blood platelet particle group A1 and leucocyte group B1 overlap with each other, affecting the leucocyte counting through the NRBC channel.

Figure 9:
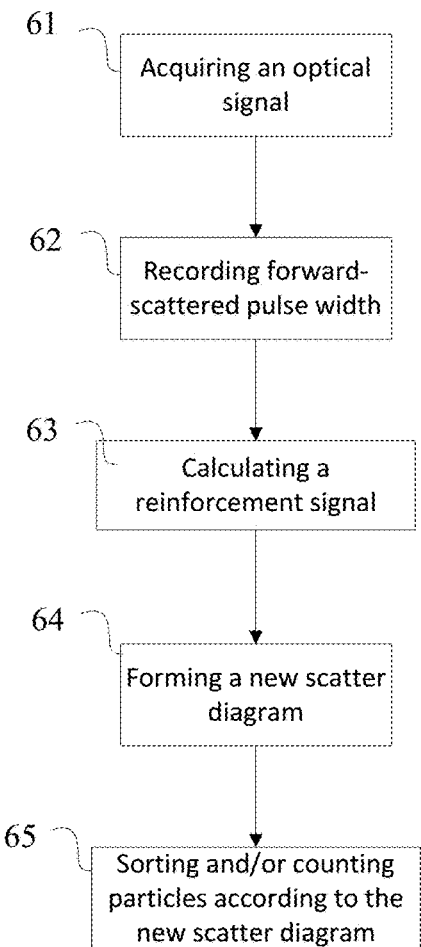
FIG. 9 is a flow diagram of NRBC channel particle sorting.

A processing method is shown in FIG. 9 In block 61, optical signals generated by particles irradiated with light in a blood sample are acquired when the sample passes through a detection region, the optical signals including forward-scattered light, side-scattered light and fluorescence. In one embodiment, the fluorescence is side fluorescence.

In block 62, a pulse width of the forward-scattered light is recorded (hereinafter referred to as forward-scattered pulse width).

In block 63, the reinforcement signal is calculated based on the pulse width. The fluorescence signal is selected as a combined optical signal, and the reinforcement signal is the product of a fluorescence signal increasing function and a pulse width increasing function, with a formula as follows:

$$Z1 = fx \cdot fy \quad (2)$$

where Z1 is a fluorescence—forward-scattered pulse width reinforcement signal, fx is an increasing function of the intensity of the fluorescence signal, and fy is an increasing function of the forward-scattered pulse width.

In some embodiments, the signal intensity of the fluorescence signal is multiplied by the forward-scattered pulse width to obtain a fluorescence—forward-scattered pulse width reinforcement signal.

Figure 10:
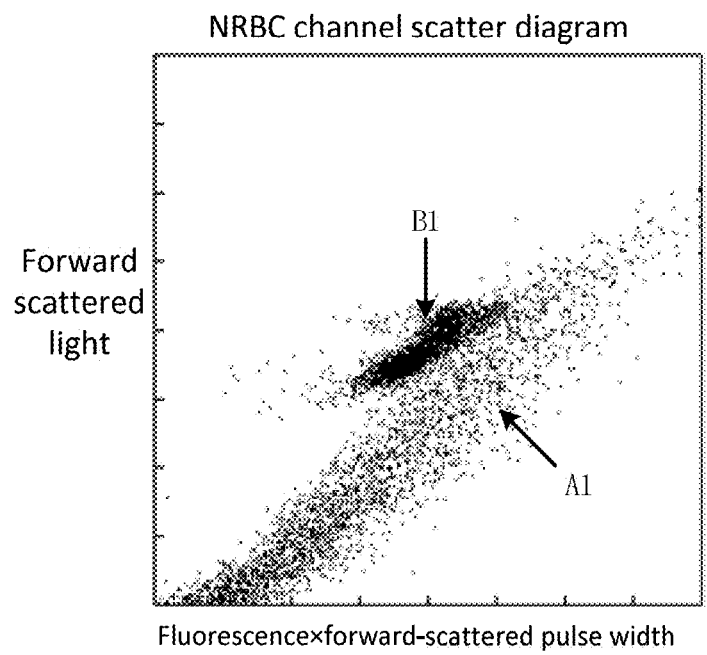
FIG. 10 is an NRBC channel scatter diagram with the fluorescence signal reinforced by the forward-scattered pulse width.

In block 64, the forward-scattered light and the fluorescence—forward-scattered pulse width reinforcement signal are selected to form a new scatter diagram. As shown in FIG. 10, the abscissa is the fluorescence—forward-scattered pulse width reinforcement signal, the ordinate is the forward-scattered light, A1 is the aggregated blood platelet particle group, and B1 is the leucocyte particle cluster.

In block 65, the particles are sorted and/or counted according to the new scatter diagram. In one embodiment, the leucocyte particles and the interfering particles are distinguished from each other according to the new scatter diagram. Typically, in the overlap region, the pulse width of the platelets tends to be greater than the pulse width of the leucocyte particles. According to FIG. 1, the aggregated blood platelet particle group A1 is located on the lower right side of the leucocyte particle cluster B1. In the direction of the fluorescence, where the forward-scattered light is the same, the fluorescence intensity of the blood platelet particles is greater than the fluorescence intensity of the leucocyte particles, or the fluorescence intensity at the center of the aggregated blood platelet particle group A1 is greater than the fluorescence intensity at the center of the leucocyte particle cluster B1. After multiplying the fluorescence intensities of the blood platelets and the leucocyte particles respectively by the pulse width, as for the multiplication of the large factors, the product will be even larger, while for the multiplication of the small factors, the product will be even smaller, the difference in the reinforcement signal between the blood platelets and the leucocyte particles is greater, and is increased relative to the difference in the fluorescence signal between the two. As shown in FIG. 10, the aggregated blood platelet particle group A1 is shifted more to the right relative to the leucocyte particle cluster B1, so that the overlap region between the aggregated blood platelet particle group A1 and the leucocyte particle cluster B1 is eliminated. Therefore, the leucocyte particles and the blood platelets can be distinguished from each other more easily and more accurately in the new scatter diagram.

Figure 11:
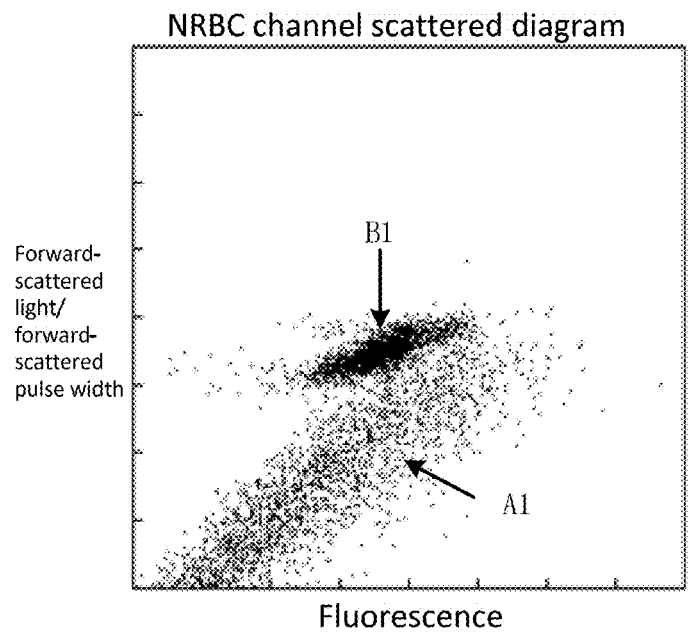
FIG. 11 is an NRBC channel scatter diagram with the forward-scattered light signal reinforced by the forward-scattered pulse width.

In block 63, the forward-scattered light may also be selected as a combined optical signal, and the reinforcement signal is a quotient of a forward-scattered light increasing function and a pulse width increasing function, for example, dividing the signal intensity of the forward-scattered light by the forward-scattered pulse width to obtain a forward-scattered—forward-scattered pulse width reinforcement signal. In block 64, the side-scattered fluorescence and the forward-scattere—forward-scattered pulse width reinforcement signal are selected to form a new scatter diagram, as shown in FIG. 11. Likewise, in the overlap region, the pulse width of the platelets is greater than the pulse width of the leucocyte particles. According to FIG. 1, in the direction of the forward-scattered light, where the fluorescence is the same, the forward-scattered light intensity of the blood platelet particles is less than the forward-scattered light intensity of the leucocyte particles, or the forward-scattered light intensity at the center of the aggregated blood platelet particle group A1 is less than the forward-scattered light intensity at the center of the leucocyte particle cluster B1. Moreover, the reinforcement signal is the forward-scattered light intensity divided by the forward-scattered pulse width, and therefore, in the new scatter diagram, the aggregated blood platelet particle group A1 will become smaller in the direction of the reinforcement signal, while the leucocyte particle cluster B1 will become greater in the direction of the reinforcement signal, so that the difference between the leucocyte particles and the aggregated blood platelet particles is greater, and the leucocyte particles and the aggregated blood platelet particles can be distinguished from each other more easily and more accurately.

That is to say, the calculation of the reinforcement signal may depend on the relative relationship between the first particle and the second particle in terms of the combined signal and the pulse width signal. For example, when the combined signals S and the pulse width signals W of the two particles A and B have the same magnitude relationship, the product is used; otherwise, the quotient is used. Specifically, if the combined signals S meet the formula SA>SB, and the pulse width signals W meet the formula WA>WB, the reinforcement signal is calculated based on the S*W, where the combined signal may be a fluorescence signal. If the combined signals S meet the formula SA<SB and the pulse width signals W meet the formula WA>WB, the reinforcement signal is calculated based on S/W, where the combined signal may be forward scattered light. In one example, when determining the magnitude relationship between the first particle and the second particle in terms of the combined signal S and the pulse width signal W, $\Delta s*\Delta w$ can be adopted. $\Delta s*\Delta w>0$ indicates that the combined signals of the two particles have the same magnitude relationship as that of the pulse width signals of the two particles, and $\Delta s*\Delta w<0$ indicates that the combined signals of the two particles have opposite magnitudes to that of the pulse width signals of the two particles. $\Delta s$ represents the difference in statistical intensities of the combined signals of the two particles, $\Delta w$ represents the difference in the statistical pulse widths of the pulse width signals of the two particles. In practice, quantitative calculations of $\Delta s$ and $\Delta w$ is not necessary. As long as it is determined whether each of $\Delta s$ and $\Delta w$ is greater than or less than zero, the manner of calculation of the reinforcement signal may be selected appropriately.

In other embodiment, the pulse width may also be the pulse width of side-scattered light or fluorescence.

Figure 12:
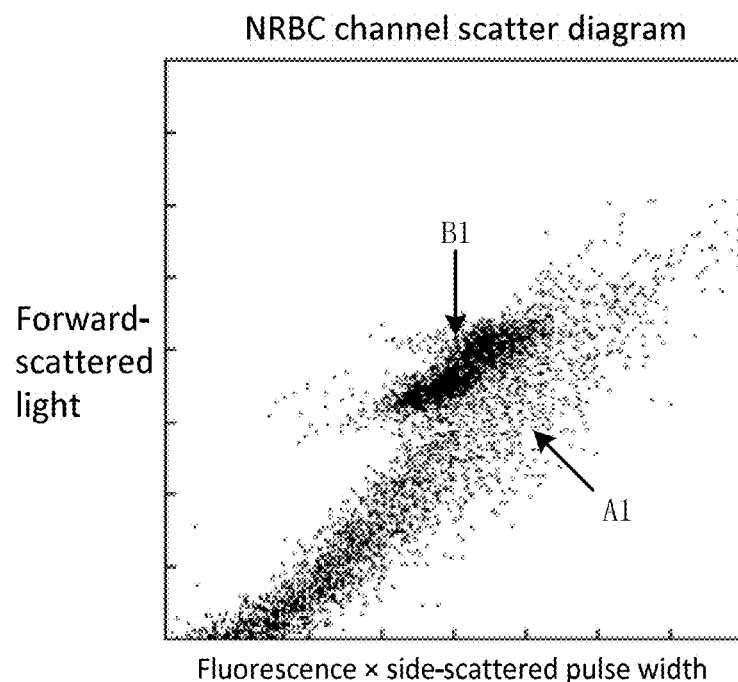
FIG. 12 is an NRBC channel scatter diagram with the fluorescence signal reinforced by the side-scattered pulse width.

As shown in FIG. 12, the pulse width is the pulse width of the side-scattered light (referred to as side-scattered pulse width), and the reinforcement signal is the product of the fluorescence and the side-scattered pulse width (referred to as fluorescence—side-scattered pulse width reinforcement signal). The forward-scattered light and the fluorescence—side-scattered pulse width reinforcement signal are selected to form a new scatter diagram. According to the new scatter diagram, the leucocyte particle cluster B1 and the aggregated blood platelet particle group A1 can also be distinguished from each other more easily and accurately.

Figure 13:
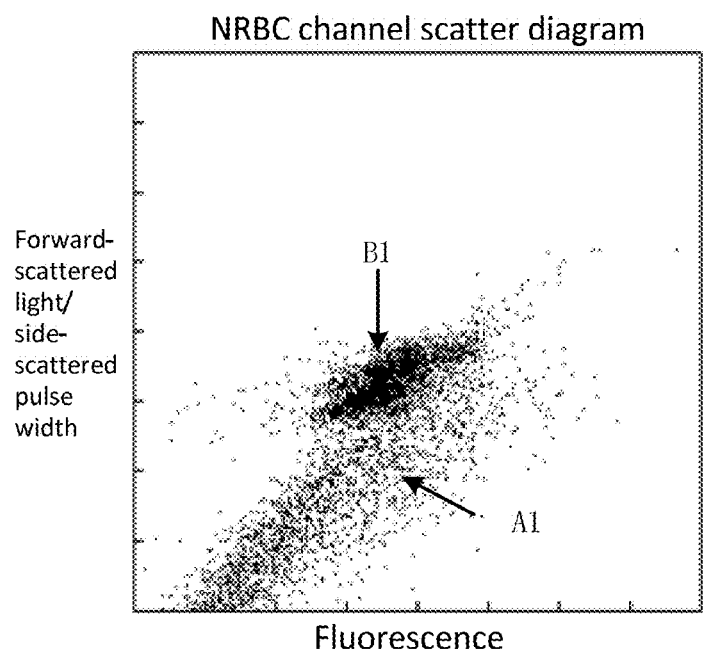
FIG. 13 is an NRBC channel scatter diagram with the forward-scattered light signal reinforced by the side-scattered pulse width.

As shown in FIG. 13, the pulse width is the pulse width of the side-scattered light (referred to as side-scattered pulse width), and the reinforcement signal is the quotient of the forward-scattered light divided by the side-scattered pulse width (referred to as forward-scattered—side-scattered pulse width reinforcement signal). The forward-scattered light—side-scattered pulse width reinforcement signal and the fluorescence are selected to form a new scatter diagram. According to the new scatter diagram, the leucocyte particle cluster B1 and the aggregated blood platelet particle group A1 can also be distinguished from each other more easily and accurately.

Figure 14:
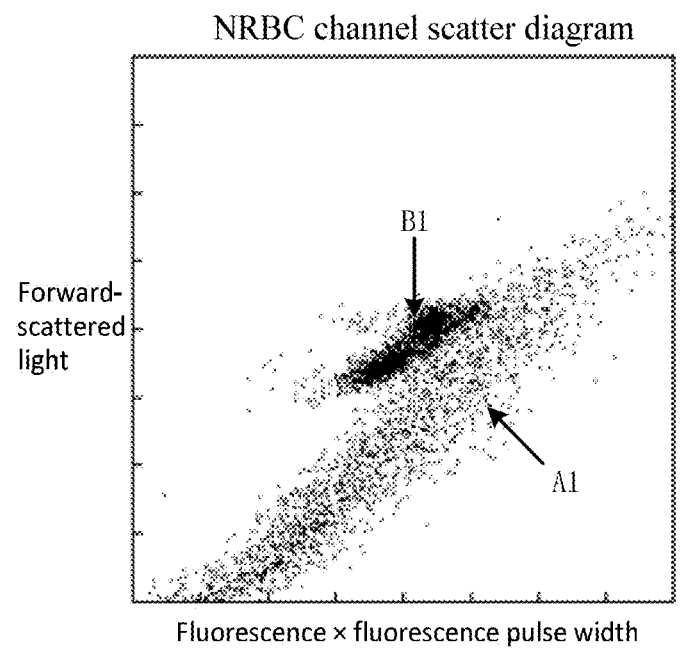
FIG. 14 is an NRBC channel scatter diagram with the fluorescence signal reinforced by the fluorescence pulse width.

As shown in FIG. 14, the pulse width is the pulse width of the fluorescence (referred to as fluorescence pulse width), and the reinforcement signal is the product of the fluorescence multiplied by the fluorescence pulse width (referred to as fluorescence—fluorescence pulse width reinforcement signal). The forward-scattered light and the fluorescence—fluorescence pulse width reinforcement signal are selected to form a new scatter diagram. According to the new scatter diagram, the leucocyte particle cluster B1 and the aggregated blood platelet particle group A1 can also be distinguished from each other more easily and more accurately.

Since the pulse signal can be regarded as an approximately triangular shape, and in one embodiment, the reinforcement signal is the product of the fluorescence multiplied by the fluorescence pulse width, the reinforcement signal can be considered to be twice the area of the fluorescent pulse signal. That is, when the combined optical signal intensity and the pulse width for calculating the reinforcement signal belong to the same optical signal, the reinforcement signal may be the area of or several times the area of the pulse signal of a certain light, which may be regarded as a special case of the reinforcement signal. In this case, it is to be understood by those skilled in the art that even if the area of or several times the area of the optical pulse signal are taken as the reinforcement signal, it should still be regarded as a combinatorial calculation of the signal intensity and pulse width of a combined optical signal. In addition, the area of the optical pulse signal can be calculated by multiplying a pulse peak value by the pulse width according to the area formula of a triangle, or by accumulating or integrating the optical signal within the pulse width.

Figure 15:
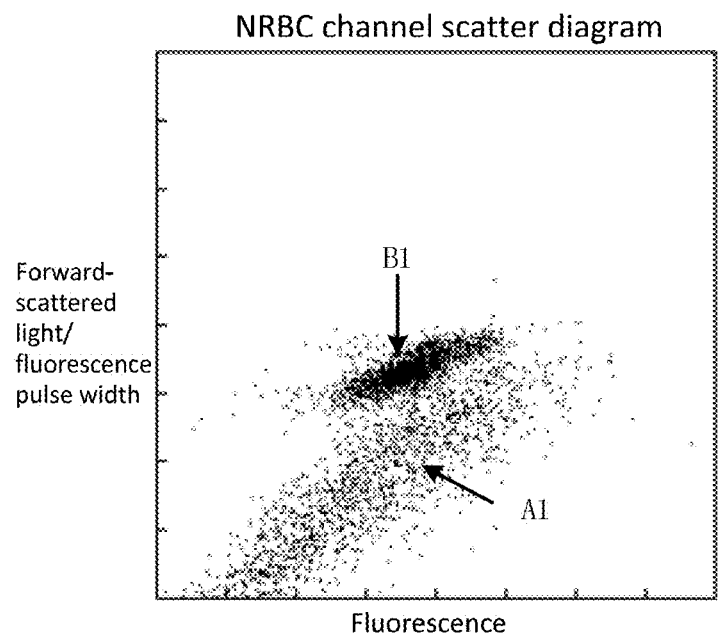
FIG. 15 is an NRBC channel scatter diagram with the forward-scattered light signal reinforced by the fluorescence pulse width.

As shown in FIG. 15, the pulse width is the pulse width of the fluorescence (referred to as fluorescence pulse width), and the reinforcement signal is the quotient of the forward-scattered light divided by the fluorescence pulse width (referred to as forward-scattered—fluorescence pulse width reinforcement signal). The forward-scattered light—fluorescence pulse width reinforcement signal and the fluorescence are selected to form a new scatter diagram. According to the new scatter diagram, the leucocyte particle cluster B1 and the aggregated blood platelet particle group A1 can also be distinguished from each other more easily and more accurately.

As those skilled in the art would understand, in this embodiment, the optical signals in the NRBC detection are used. In the forward-scattered light signal-fluorescence signal scatter diagram, NRBC can be distinguished from the leucocytes, and the NRBC count and the leucocyte count may be acquired respectively.

In another embodiment, a lipid granule sample is taken as an example. The blood sample was measured by a blood cell analyzer, and a leucocyte count is obtained through a BASO channel.

Figure 16:
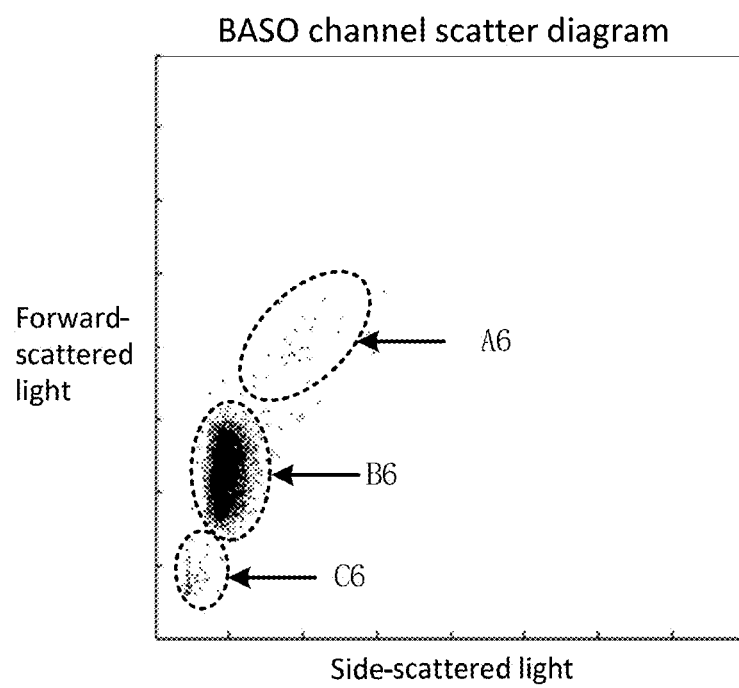
FIG. 16 is a BASO channel scatter diagram of the normal sample.

There is no lipid granules in a normal sample in the BASO channel, so that the leucocyte count is accurate. A BASO channel scatter diagram of a normal sample is shown in FIG. 16, where the abscissa is the side-scattered light signal, the ordinate is the forward-scattered light signal. B6 is leucocytes other than basophil granulocytes, namely lymphocytes, monocytes, neutrophil granulocytes and eosinophil granulocytes, being a main leucocyte cluster. A6 is basophil granulocytes; C6 is blood ghost, that is, fragments of red blood cells and platelets after treatment with a hemolytic agent. As can be seen from FIG. 16, there is few blood ghost spots in the normal sample, and the blood ghost are located below the main leucocyte cluster and greatly separated from the main leucocyte cluster, so that the leucocyte counting will not be interfered with.

Figure 2:
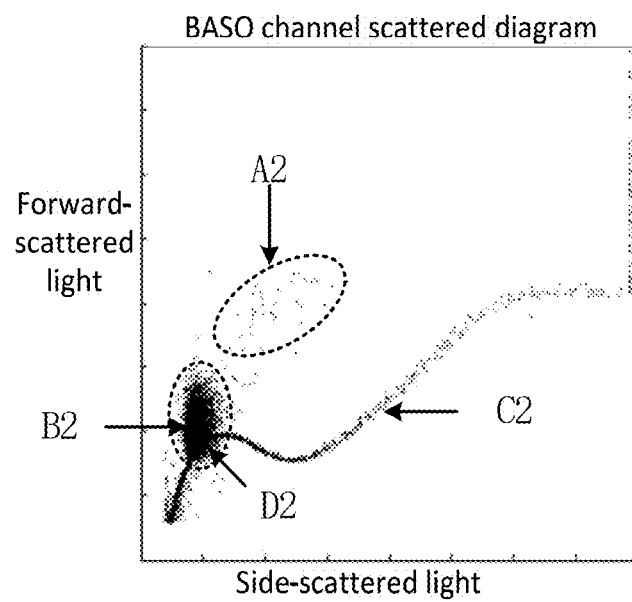
FIG. 2 is a BASO channel scatter diagram of a lipid granule sample.

When there are lipid granules in the blood sample, an S-shaped curve will be formed in the BASO channel, as shown in FIG. 2, where the abscissa is the side-scattered light signal, and the ordinate is the forward-scattered light signal. B2 is leucocytes other than basophil granulocytes, namely lymphocytes, monocytes, neutrophil granulocytes and eosinophil granulocytes, being a main leucocyte cluster. A2 is basophil granulocytes; C2 is blood ghost, that is, fragments of red blood cells and platelets after treatment with a hemolytic agent. In particular, at the lower end of the side-scattered light signal and the forward-scattered light signal, the lipid granules overlap with the leucocyte group and affect the leucocyte counting. Consequently, the leucocytes and the lipid granules cannot be distinguished from each other by the side-scattered light and forward-scattered light signals.

Figure 17:
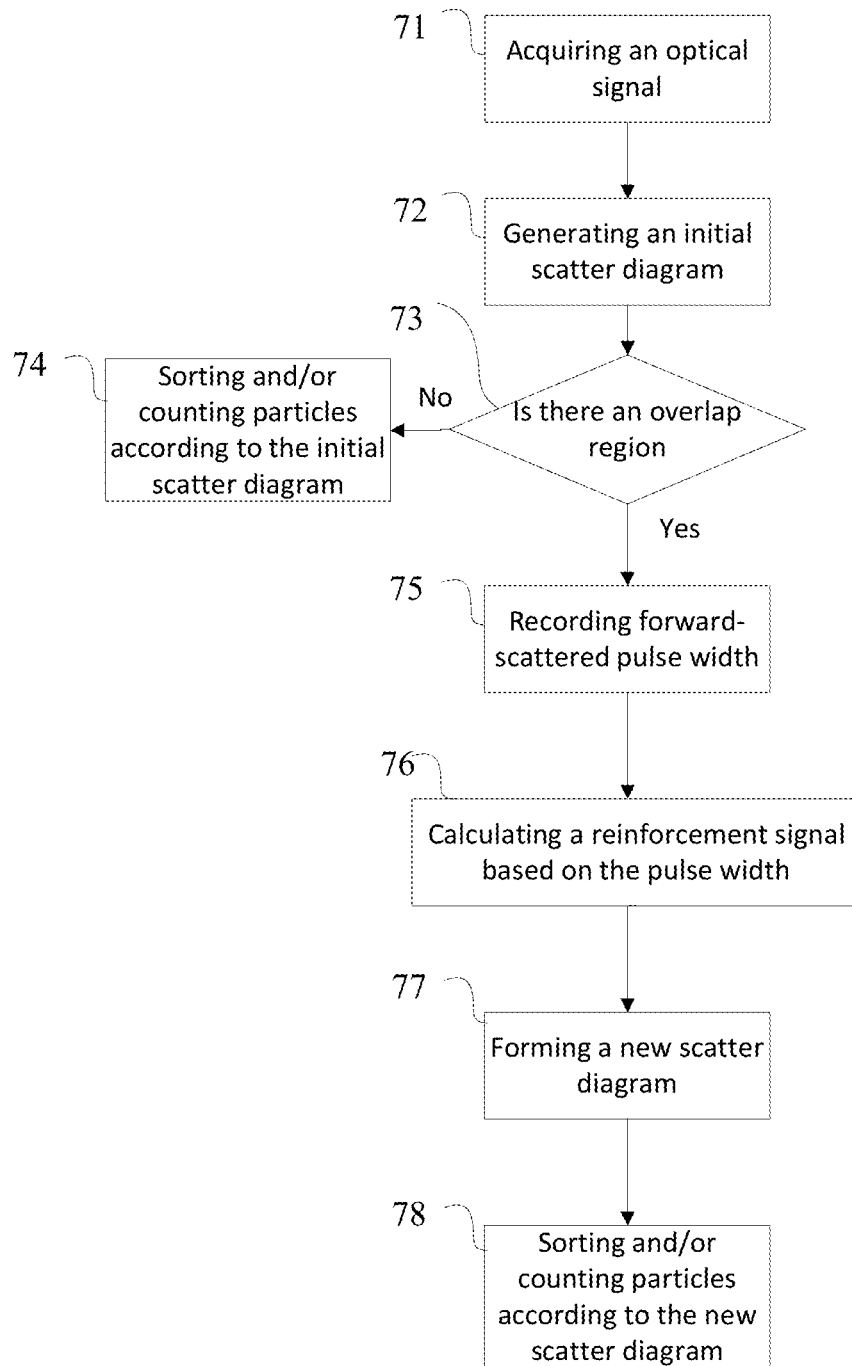
FIG. 17 is a flow diagram of BASO channel particle sorting.

To reduce the influence of lipid granules on the leucocyte counting, a processing procedure of one embodiment is shown in FIG. 17 In block 71, optical signals generated by particles irradiated with light in a blood sample are acquired when the sample passes through a detection region for detection, the optical signals including forward-scattered light and side-scattered light.

In block 72, an initial scatter diagram is generated according to the forward-scattered light and the side-scattered light, where the abscissa is the side-scattered light, and the ordinate is the forward-scattered light.

In block 73, it is determined whether there is an overlap region between lipid granules and a leucocyte group in the initial scatter diagram. If there is no overlap region between lipid granules and a leucocyte group in the initial scatter diagram, as shown in FIG. 16, block 74 is performed; and if there is an overlap region between lipid granules and a leucocyte group in the initial scatter diagram, as shown in FIG. 2, block 75 is performed.

In block 74, sorting and/or counting the leucocytes is performed according to the initial scatter diagram.

In block 75, a pulse width of the forward-scattered light is recorded (hereinafter referred to as forward-scattered pulse width).

In block 76, the reinforcement signal is calculated based on the pulse width. The forward-scattered light is selected as a combined optical signal; the reinforcement signal is the product of a forward-scattered light increasing function and a pulse width increasing function. In some embodiments, the intensity of the forward-scattered light signal is multiplied by the forward-scattered pulse width to obtain a forward-scattered light—forward-scattered pulse width reinforcement signal.

Figure 18:
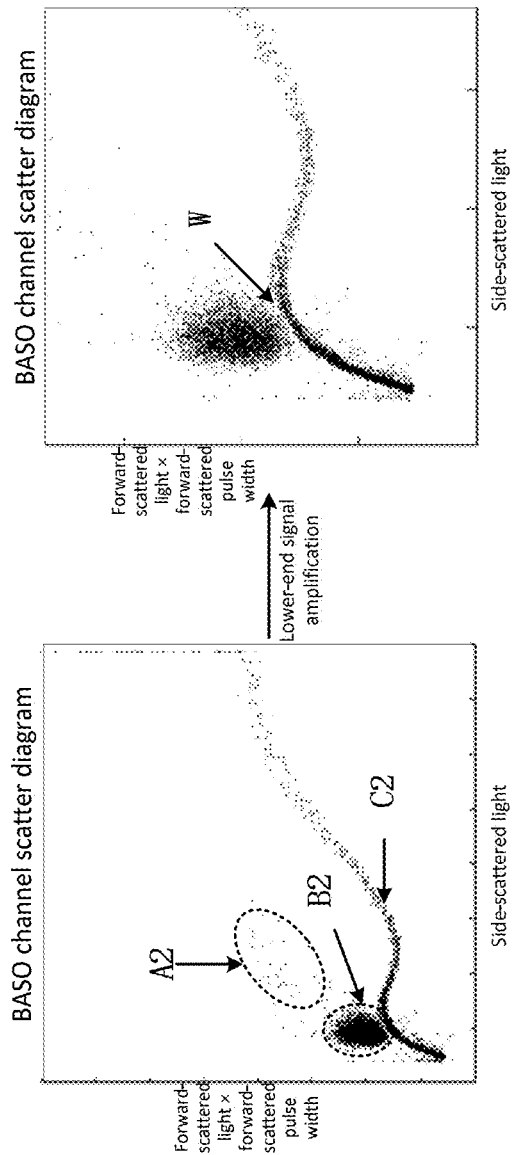
FIG. 18 is a BASO channel scatter diagram with the forward-scattered light signal reinforced by the forward-scattered pulse width.

In block 77, the side-scattered light and the forward-scattered light—forward-scattered pulse width reinforcement signal are selected to form a new scatter diagram. As shown in FIG. 18, the abscissa is the side-scattered light, the ordinate is the forward-scattered light—forward-scattered pulse width reinforcement signal, A2 is a basophil granulocyte cluster, B2 is a main leucocyte cluster, and C2 is lipid granules.

In block 78, the particles are sorted and/or counted according to the new scatter diagram. In one embodiment, the leucocyte particles and the interfering particles are distinguished from each other according to the new scatter diagram. As shown in FIG. 2, in the region D2 where the lipid granules overlap with the leucocyte group, the lipid granules are located on the lower right side of the main leucocyte cluster B2. In the direction of the forward-scattered light, where the side-scattered light is the same, the forward-scattered light intensity of the lipid granules is less than the forward-scattered light intensity of the leucocyte particles. As shown in FIGS. 4A and 4B, at the lower end of the forward-scattered light signal, the pulse width of the lipid granules A4 is smaller than the pulse width of the main leucocyte cluster C4.

After multiplying the forward-scattered light intensities of the lipid granules and the leucocyte particles respectively by the pulse width, as for the multiplication of the large factors, the product will be even larger, while for the multiplication of the small factors, the product will be even smaller, the difference in the reinforcement signal between the lipid granules and leucocyte particles is greater, and the distance is increased relative to the difference in the forward-scattered light signal between the two. As shown in FIG. 18, the lipid granules C2 are shifted more to the lower right side relative to the main leucocyte cluster B2, such that there is already an apparent empty space W between the lipid granules C2 and the main leucocyte cluster B2, as shown in an enlarged view on the right side of FIG. 18. Therefore, the overlap between the lipid granules and the leucocyte cluster is avoided in the new scatter diagram, so that the leucocyte particles and the lipid granules can be distinguished from each other more easily and more accurately, thus facilitating the sorting.

In one embodiment, it is also possible not to determine whether or not there is an overlap region according to an initial scatter diagram, and instead, block 75 is performed directly after block 71.

Figure 19:
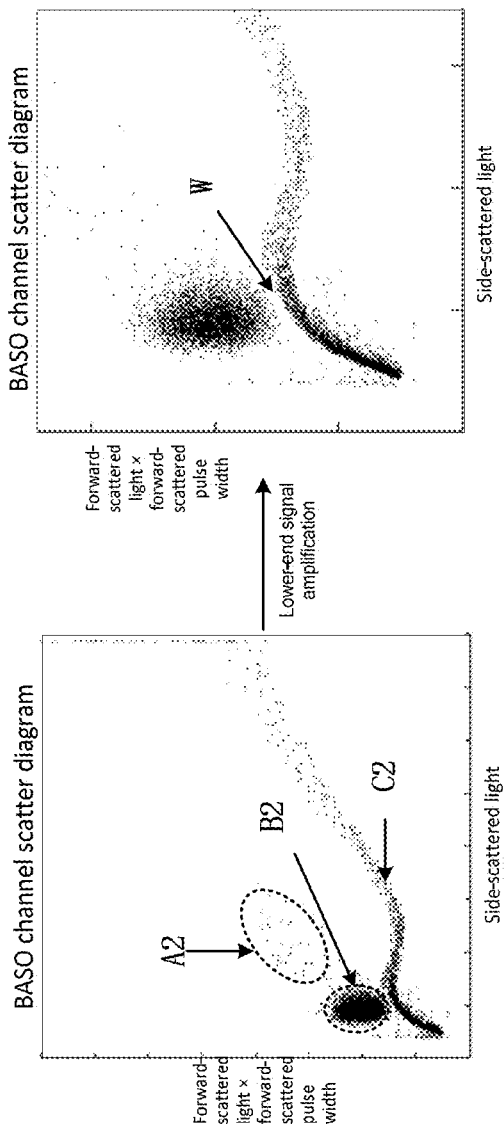
FIG. 19 is a BASO channel scatter diagram with the forward-scattered light signal reinforced by the square of the forward-scattered pulse width.

In block 76, after selecting the forward-scattered light as a combined optical signal, the intensity of the forward-scattered light signal may also be multiplied by the forward-scattered pulse width to the power of N (N is greater than 1) to obtain a forward-scattered light—forward-scattered pulse width reinforcement signal, for example, multiplying the intensity of the forward-scattered light signal by the square of the forward-scattered pulse width to obtain a reinforcement signal. A new scatter diagram is formed by the side-scattered light and the reinforcement signal. As shown in FIG. 19, the lipid granules C2 are shifted more to the lower right side relative to the main leucocyte cluster B2, such that there is already an apparent empty space W between the lipid granules C2 and the main leucocyte cluster B2, as shown in an enlarged view on the right side of FIG. 19. Therefore, the leucocyte particles and the lipid granules can also be distinguished from each other more easily and more accurately according to the new scatter diagram.

In other embodiments, the abscissa and the ordinate of the new scatter diagram may be different reinforcement signals. For example, the abscissa is a side-scattered—forward-scattered pulse width reinforcement signal, and the ordinate is a forward-scattered—forward-scattered pulse width reinforcement signal.

In a further embodiment, the pulse width may also be the pulse width of the side-scattered light. In block 76, the forward-scattered light may also be selected as a combined optical signal, and the reinforcement signal is a product of a forward-scattered light increasing function and a side-scattered pulse width increasing function, for example, multiplying the signal intensity of the forward-scattered light by the side-scattered pulse width to obtain a forward-scattered—side-scattered pulse width reinforcement signal. In block 77, the side-scattered fluorescence and the forward-scattered—side-scattered pulse width reinforcement signal are selected to form a new scatter diagram, where the main leucocyte cluster is shifted more to the upper left side relative to the lipid granules, such that the leucocyte particles and the lipid granules can also be distinguished from each other.

According to the above disclosure, it is to be understood by those skilled in the art that the reinforcement signal may be a function of the combined optical signal and the pulse width in order to obtain a scatter diagram that can distinguish between the leucocyte particles and the interfering particles, so long as the function increases the difference in the reinforcement signal between the leucocyte particles and the interfering particles relative to the difference between the two in the combined optical signal.

The above embodiments illustrate the distinguishing between leucocytes and lipid granules or aggregated PLT particles. According to the disclosed in the present application, it is to be understood by those skilled in the art that for two different categories of particles, if they differ in size in the overlap region, i.e., there are a difference in the pulse width between the two categories of particles in the overlap region, the above embodiments can also be used to distinguish between the two categories of particles, for example, a routine test for five types of leucocytes in certain scenes. When there is an overlap region between two categories of particles, such as lymphocytes and a monocyte cluster having an overlap region, according to different pulse widths of the particles of the lymphocytes and the monocyte cluster in the overlap region, a new reinforcement signal can also be formed using functions of an optical signal and a pulse width signal, and the lymphocytes and monocytes can be distinguished from each other based on a scatter diagram generated by the reinforcement signal, thereby obtaining a more accurate result of the five types.

The foregoing embodiments are described by taking the NRBC and BASO channels commonly used in cell analyzers as examples. Those skilled in the art will appreciate that in a leucocyte classification channel (DIFF channel), it is also possible to distinguish between two categories of overlapping particles by using the method described above. Specifically, in the blood sample treated with the reagent, red blood cells are dissolved, each of cell particles in the sample liquid emits scattered lights after being irradiated by the light beam, and forward-scattered lights, side-scattered light, and/or medium-angle-scattered light signal are collected. Based on at least two types of scattered lights, leucocytes can be classified into four types of particles, i.e., lymphocytes, monocytes, neutrophils, eosinophils, namely the leucocyte four classification (DIFF). It will be appreciated that leucocytes and aggregated platelet particles or lipid particles can be distinguished from each other by a new scatter diagram including the reinforcement signal acquired by using the foregoing methods. In another case, in the blood sample treated with the reagent, the red blood cells are dissolved, the cells are stained with a fluorescent dye, and the particles in the sample liquid are irradiated by the light beam, such that fluorescent signals, forward scattered light, and/or side scattered light are collected. Based at least on fluorescent signals and side-scattered light signals, leucocytes can also be classified into four types of particles, i.e., lymphocytes, monocytes, neutrophils, and eosinophils. Also, leucocyte particles and aggregated platelet particles or lipid particles can be distinguished by a new scatter diagram including the reinforcement signal acquired by using the foregoing method.

In the foregoing embodiments, the reinforcement signal is calculated based on a product or a quotient between the combined signal and the pulse width signal. In other embodiments, instead of the product, the reinforcement signal is calculated based on a monotonic increasing function of the combined optical signal and a monotonic increasing function of the pulse width signal, or, the reinforcement signal is calculated based on a monotonic decreasing function of the combined optical signal and a monotonic decreasing function of the pulse width signal; or, instead of the quotient, the reinforcement signal is calculated based on a monotonic increasing function of one of the combined optical signal and the pulse width signal and a monotonic decreasing function of the other one.

It is to be understood by those skilled in the art that all or some of the blocks of the various cell analyzers in the embodiments described above could be achieved by special purpose hardware or by a general purpose processor executing instructions stored in a computer-readable storage medium. The storage medium may include a read-only memory, a random access memory, a magnetic disk, or an optical disk, or the like.

In addition, at least some of the function units in the above embodiment of the application may be integrated into a processor. When being realized in form of software function unit and sold or used as an independent product, the function may also be stored in a computer-readable storage medium. Based on such an understanding, the technical solutions of the application substantially or parts making contributions to the conventional art or part of the technical solutions may be embodied in form of software product, and the computer software product is stored in a storage medium, including a plurality of instructions configured to enable a processor (which may be the data processing apparatus in the cell analyzer, or may be in a computer connected to the cell analyzer) to execute all or part of the operations of the method in each embodiment of the application. The above-mentioned storage medium includes: various media capable of storing program codes such as a U disk, a mobile hard disk, a Read-Only Memory (ROM), a Random Access Memory (RAM), a magnetic disk or an optical disk.

The present disclosure has been set forth with reference to specific examples, which are merely for the purpose of facilitating the understanding of the present disclosure and are not intended to limit the same. It will be apparent to those of ordinary skill in the art that changes may be made to the specific embodiments described above in accordance with the teachings of the present disclosure.

What is claimed is:

1. A cell analyzer, comprising:
  a reaction chamber, that provides a location for reaction between a blood sample and a reagent to get a sample liquid;
  a flow chamber having a detection region, through which the sample liquid pass in sequence with shrouding by a sheath liquid;
  a conveying apparatus having a conveying line and a control valve, wherein the sample liquid is conveyed into the flow chamber through the conveying line;
  an optical detection apparatus having a plurality of optical signal detectors, operable to collect multiple optical signals generated by each of particles irradiated with light in a blood sample in a detection region, the particles comprising a first category of particles and a second category of particles; and
  a data processing apparatus, configured to:
  for each of the particles, acquire intensities of a first group of optical signals, which comprise at least two optical signals selected from the multiple optical signals, and a pulse width of a second group of optical signals, which comprises at least one optical signal selected from the multiple optical signals;
    for each of the particles, calculate one or more reinforcement signals related to the particle, each reinforcement signal comprising a reinforcement signal based on an intensity of a first optical signal selected from the first group of optical signals and a pulse width of a second optical signal selected from the second group of optical signals, wherein the first optical signal is as same as or different from the second optical signal; and
    distinguish between the first category of particles and the second category of particles based at least partially on the one or more reinforcement signals related to each of the particles.

2. The cell analyzer of claim 1, wherein the data processing apparatus is configured to:
  generate a first scatter diagram for the particles, based on the one or more reinforcement signals and an intensity of at least one optical signal, other than the first optical signal associated with any of the one or more reinforcement signals, selected from the first group of optical signals; and
  distinguish between the first category of particles and the second category of particles based on the first scatter diagram.

3. The cell analyzer of claim 1, wherein the plurality of optical signal detectors comprise at least two scattered light detectors selected from a forward-scattered light detector for collecting a forward-scattered light signal, a side-scattered light detector for collecting a side-scattered light signal, and a medium-angle-scattered light detector for collecting a medium-angle-scattered light signal, and
  wherein each of the first optical signal and the second optical signal is selected from the forward-scattered light signal, the side-scattered light signal, and the medium-angle-scattered light signal independently.

4. The cell analyzer of claim 3, wherein at least one of the first optical signal or the second optical signal is the forward-scattered light signal.

5. The cell analyzer of claim 3, wherein the data processing apparatus is configured to calculate the reinforcement signal based on an intensity of the forward-scattered light signal as the first optical signal and a pulse width of the forward-scattered light signal as the second optical signal.

6. The cell analyzer of claim 5, wherein the first category of particles are leucocyte particles, and the second category of particles are lipid granules or blood platelet (PLT) particles,
  wherein the data processing apparatus is configured to distinguish between the first category of particles and the second category of particles based on the reinforcement signal related to each of the particles and the intensity of the side-scattered light signal of the respective particle.

7. The cell analyzer of claim 3, wherein the plurality of optical signal detectors comprise a front-scattered light detector for collecting a front-scattered light signal, and at least one of a side-scattered light detector for collecting a side-scattered light signal or a medium-scattered light detector for collecting a medium-scattered light signal, and
  wherein the data processing apparatus is further configured to:
  distinguish leucocyte particles into lymphocytes, monocytes, neutrophil granulocytes and eosinophil granulocytes based on the forward-scattered light signal and the side-scattered light signal of each of the particles; or
  distinguish leucocyte particles into lymphocytes, monocytes, neutrophil granulocytes and eosinophil granulocytes based on the forward-scattered light signal and the medium-angle-scattered light signal of each of the particles.

8. The cell analyzer of claim 1, wherein the plurality of optical signal detectors comprise a fluorescence detector for collecting a fluorescence signal and at least one scattered light detector for collecting a respective scattered light signal, and
  wherein the data processing apparatus is further configured to calculate the reinforcement signal based on the fluorescence signal and at least one of the scattered light signal.

9. The cell analyzer of claim 8, wherein the first category of particles are leucocyte particles, and the second category of particles are aggregated platelet (PLT) particles.

10. The cell analyzer of claim 8, wherein the at least one scattered signal comprises a forward-scattered light signal and a side-scattered light signal, and
  wherein distinguishing between the first category of particles and the second category of particles comprises:
  generating a first scatter diagram at least based on the reinforcement signal and a third optical signal selected from the first group of optical signals; and
  distinguishing between the first category of particles and the second category of particles based on the first scatter diagram,
  wherein each of the first optical signal, the second optical signal, and the third optical signal is different from one another, or each of the first optical signal, the second optical signal, and the third optical signal is selected from the fluorescence signal and the forward-scattered light signal.

11. The cell analyzer of claim 1, wherein the plurality of optical signal detectors comprise a fluorescence detector for collecting a fluorescence signal, and a forward-scattered light detector for collecting a forward-scattered light signal; and wherein the data processing apparatus is further configured to:

generate a second scatter diagram based on the fluorescence signal and the forward-scattered light signal of each of the particles; and count nucleated red blood cells based on the second scatter diagram.

12. The cell analyzer of claim 1, wherein the plurality of optical signal detectors comprise a fluorescence detector for collecting a fluorescence signal, and a side-scattered light detector for collecting a side-scattered light signal; and wherein the data processing apparatus is further configured to:

distinguish leucocyte particles into lymphocytes, monocytes, neutrophil granulocytes and eosinophil granulocytes, based on the fluorescence signal and the side-scattered light signal of each of the particles.

13. The cell analyzer of claim 1, after acquiring the intensities of the first group of optical signals, the data processing apparatus is further configured to generate a third scatter diagram based on the intensities of the first group of optical signals of each of the particles; and wherein for each of the particles, data processing apparatus acquires the pulse width of the second group of optical signals when there is an overlap region of a cluster of the first category of particles and a cluster of the second category of particles in the third scatter diagram, to calculate the one or more reinforcement signals.

14. The cell analyzer of claim 1, wherein the reagent contains a hemolytic agent, and red blood cells are dissolved into blood ghost particles.

15. The cell analyzer of claim 1, wherein the reinforcement signal is a non-linear combination function of the intensity of the first optical signal and the pulse width of the second optical signal, or the reinforcement signal is a monotonic function of the intensity of the first optical signal and the pulse width of the second optical signal.

16. The cell analyzer of claim 1, wherein when $\Delta s * \Delta w$ is greater than zero, the reinforcement signal is a monotonic increasing function or a monotonic decreasing function of the intensity of the first optical signal and the pulse width of the second optical signal; or when $\Delta s * \Delta w$ is less than zero, the reinforcement signal is a monotonic increasing function of the intensity of the first optical signal and a monotonic decreasing function of the pulse width of the second optical signal, or the reinforcement signal is a monotonic decreasing function of the intensity of the first optical signal and a monotonic increasing function of the pulse width of the second optical signal, wherein $\Delta s$ represents a difference between a statistical intensity of the first optical signals of the first category of particles and that of the first optical signals of the second category of particles, and $\Delta w$ represents a difference between a statistical pulse width of the second optical signals of the first category of particles and that of the second optical signals of the second category of particles.

17. The cell analyzer of claim 1, further comprising:

a light source, operable to radiate the blood sample in the detection region with light; and a photoelectric sensor, operable to convert the collected optical signals to electric signals and output the electric signals to the data processing apparatus.

18. A non-transitory computer readable storage medium, in which instructions are stored, wherein the instructions, when executed by a processor, cause the processor to execute a method, comprising:

collecting multiple optical signals generated by each of particles irradiated with light in a blood sample in a detection region, the particles comprising a first category of particles and a second category of particles;

for each of the particles, acquiring intensities of a first group of optical signals, which comprise at least two optical signals selected from the multiple optical signals, and a pulse width of a second group of optical signals, which comprises at least one optical signal selected from the multiple optical signals;

for each of the particles, calculating one or more reinforcement signals related to the particle, based on an intensity of a first optical signal selected from the first group of optical signals and a pulse width of a second optical signal selected from the second group of optical signals, wherein the first optical signal is as same as or different from the second optical signal; and distinguishing between the first category of particles and the second category of particles based at least partially on the one or more reinforcement signals related to each of the particles.

* * * * *